US012588880B2

(12) United States Patent
Koeda et al.

(10) Patent No.: US 12,588,880 B2
(45) Date of Patent: Mar. 31, 2026

(54) PORTABLE RADIOGRAPHIC IMAGING APPARATUS AND RADIOGRAPHIC IMAGING SYSTEM

(71) Applicant: Konica Minolta, Inc., Tokyo (JP)

(72) Inventors: Keisuke Koeda, Higashimurayama (JP); Takeshi Nukanobu, Hachioji (JP); Nobuyuki Miyake, Yokohama (JP); Hiroaki Nakano, Sagamihara (JP); Katsumi Oshida, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 240 days.

(21) Appl. No.: 18/301,585

(22) Filed: Apr. 17, 2023

(65) Prior Publication Data

US 2023/0380784 A1 Nov. 30, 2023

(30) Foreign Application Priority Data

May 31, 2022 (JP) ................................. 2022-088141

(51) Int. Cl.
*A61B 6/00* (2024.01)
(52) U.S. Cl.
CPC .................................. *A61B 6/4405* (2013.01)
(58) Field of Classification Search
CPC ... A61B 6/4233; A61B 6/4283; A61B 6/4405; A61B 6/56
See application file for complete search history.

(56) References Cited

U.S. PATENT DOCUMENTS

| | | | | |
|---|---|---|---|---|
| 12,306,356 B2 * | 5/2025 | Shen | ........................ | G01T 1/175 |
| 2012/0250825 A1 * | 10/2012 | Yoshida | ................... | A61B 6/56 |
| | | | | 378/91 |
| 2014/0254756 A1 * | 9/2014 | Tagawa | ................. | H01R 13/62 |
| | | | | 378/189 |

FOREIGN PATENT DOCUMENTS

| | | |
|---|---|---|
| JP | 2011143125 A | 7/2011 |
| JP | 2012208337 A | 10/2012 |
| JP | 2013096762 A | 5/2013 |

OTHER PUBLICATIONS

Office Action (Notice of Reasons for Refusal) issued on Dec. 2, 2025, by the Japanese Patent Office in corresponding Japanese Patent Application No. 2022-088141, and a machine English Translation of the Office Action. (7 pages).
Office Action (Notice of Reasons of Refusal) issued on Feb. 17, 2026, by the Japanese Patent Office in corresponding Japanese Patent Application No. JP 2022-088141, and a machine English Translation of the Office Action (4 pages).

* cited by examiner

*Primary Examiner* — Dani Fox
(74) *Attorney, Agent, or Firm* — Buchanan Ingersoll & Rooney PC

(57) ABSTRACT

A portable radiographic imaging apparatus includes a plurality of connectors to which respective wiring cables are connectable, wherein the plurality of connectors include at feast a first connector that supports a generic communication cable, and a second connector that supports a non-generic communication cable.

6 Claims, 5 Drawing Sheets

LEFT ⟷ UPWARD

DOWNWARD ⟷ RIGHT

2

2A

21

22

100 (TYPE A)

1

12

11
GENERATOR

13

DEDICATED CABLE FOR SYNCHRONIZATION

DEDICATED CABLE FOR SYNCHRONIZATION

3
CONSOLE

4
SYNCHRONIZATION CONTROL DEVICE

5
CONVERTER

2

22

PORTABLE RADIOGRAPHIC IMAGING APPARATUS

X

LAN CABLE (COMMUNICATION)

LAN CABLE (COMMUNICATION)

PS

POWER SOURCE

NON-GENERIC COMMUNICATION CABLE (SYNCHRONIZATION + COMMUNICATION + POWER SUPPLY)

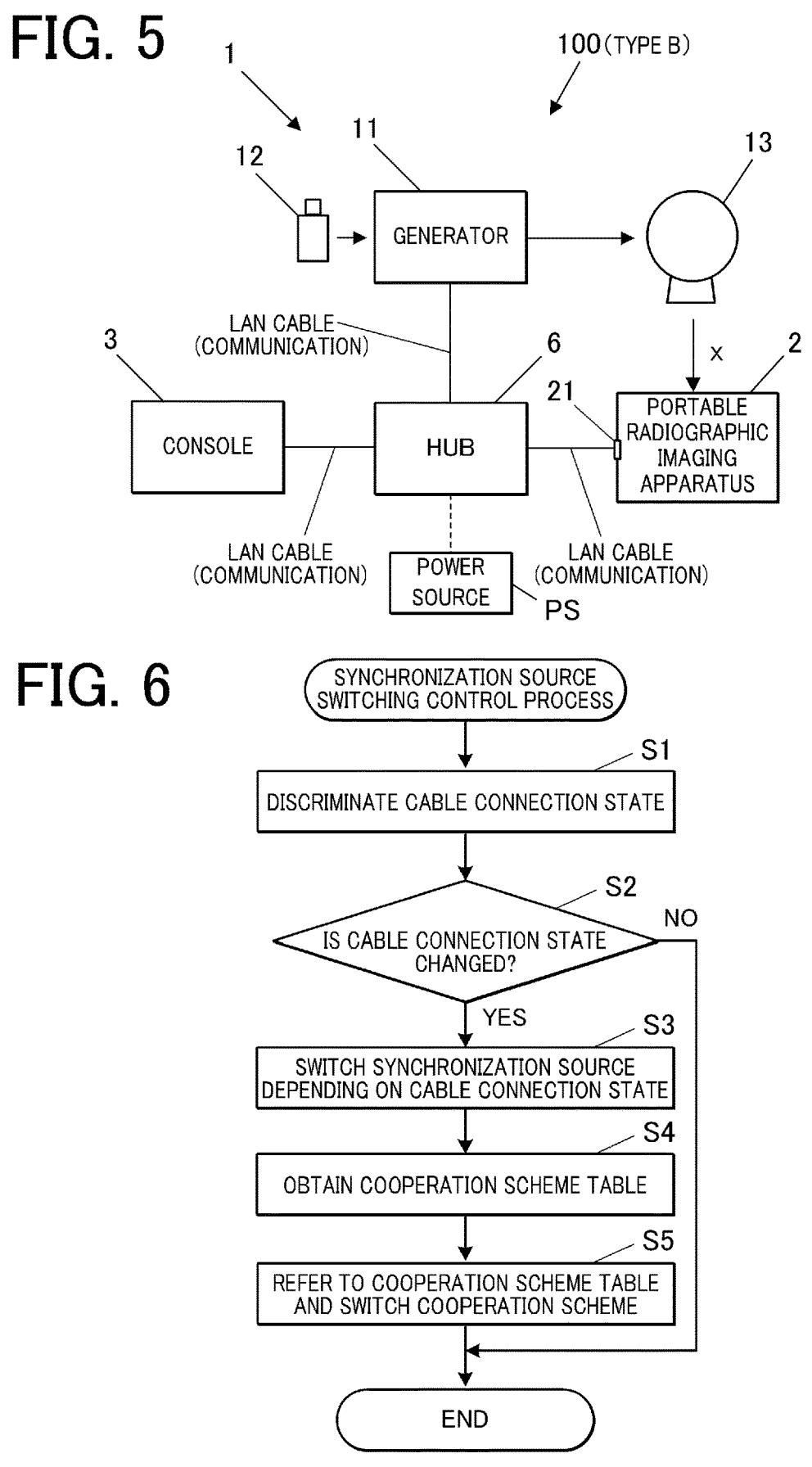

100 (TYPE B)

12

11

GENERATOR

13

LAN CABLE
(COMMUNICATION)

3

6

21

2

X

CONSOLE

HUB

PORTABLE
RADIOGRAPHIC
IMAGING
APPARATUS

LAN CABLE
(COMMUNICATION)

POWER
SOURCE

PS

LAN CABLE
(COMMUNICATION)

FIG. 6

SYNCHRONIZATION SOURCE
SWITCHING CONTROL PROCESS

S1

DISCRIMINATE CABLE CONNECTION STATE

S2

NO

IS CABLE CONNECTION STATE
CHANGED?

YES

S3

SWITCH SYNCHRONIZATION SOURCE
DEPENDING ON CABLE CONNECTION STATE

S4

OBTAIN COOPERATION SCHEME TABLE

S5

REFER TO COOPERATION SCHEME TABLE
AND SWITCH COOPERATION SCHEME

END

| SYNCHRONIZATION SOURCE | COOPERATION SCHEME |
|---|---|
| SYNCHRONIZATION CONTROL DEVICE (TYPE A) | HARDWARE SCHEME |
| CONSOLE (TYPE B) | SOFTWARE SCHEME |

FIG. 9

100 (TYPE C)

PORTABLE RADIOGRAPHIC IMAGING APPARATUS AND RADIOGRAPHIC IMAGING SYSTEM

CROSS-REFERENCE TO RELATED APPLICATIONS

The entire disclosure of Japanese Patent Application No. 2022-088141 filed May 31, 2022 is incorporated herein by reference in its entirety.

TECHNICAL FIELD

The present invention relates to a portable radiographic imaging apparatus, and a radiographic imaging system.

DESCRIPTION OF THE RELATED ART

Conventionally, a radiographic imaging apparatus (hereinafter referred to as a portable radiographic imaging apparatus) that is called a flat panel detector (FPD) has been used for taking a radiograph. Many of the portable radiographic imaging apparatuses include connectors each uniquely designed on a maker-by-maker basis. This is because as disclosed in JP 2011-143125A, a holding structure that prevents a cable from being easily detached from the connector, a high power supply efficiency to the apparatus itself, and high-speed communication with an external apparatus are intended to be securely achieved at the same time. Thus, many of portable radiographic imaging apparatuses include non-generic connectors. Accordingly, the apparatuses are used with non-generic communication cables that support the connectors in a combined manner.

Incidentally, the radiographic imaging system includes not only the portable radiographic imaging apparatus, but also peripheral devices, such as a communication (charging) IF cable, a HUB and a synchronization control device. Consequently, introduction of the radiographic imaging system causes a cost including all the devices described above as system cost items. Accordingly, small-sized clinics, medical institutions in developing countries and the like demand to reduce the system cost. To meet such a demand, a method is disclosed that reduces the system cost by arranging a connector supporting a generic communication cable (a USB cable etc.) in a portable radiographic imaging apparatus, and by constituting the system with the generic communication cable (for example, JP 2013-096762A).

SUMMARY OF THE INVENTION

Existing users having already constructed radiographic imaging systems using non-generic communication cables cannot connect cables to portable radiographic imaging apparatuses disclosed in JP 2013-096762A described above, and are required to reconstruct cables and peripheral devices. Consequently, use of the portable radiographic imaging apparatuses cause additional system cost items.

An existing user's system that is a product through collaboration and cooperation between companies due to B2B (Business to Business) having increased in recent years causes problems of difficulty in changing hardware owing to a designed rate limitation by the companies and incapability of connection of a portable radiographic imaging apparatus that includes a connector supporting a generic communication cable.

The present invention has been made in view of the above problems, and has an object to allow a portable radiographic imaging apparatus to be used with a system using a generic communication cable and also with a system using a non-generic communication cable.

To achieve at least one of the abovementioned objects, according to an aspect of the present invention, a portable radiographic imaging apparatus reflecting one aspect of the present invention, includes:
  a plurality of connectors to which respective wiring cables are connectable,
  wherein the plurality of connectors include at least a first connector that supports a generic communication cable, and a second connector that supports a non generic communication cable.

To achieve at least one of the abovementioned objects, according to an aspect of the present invention, radiographic imaging system reflecting one aspect of the present invention, includes:
  a radiation irradiation apparatus that includes a radiation source that generates radiation according to a control signal from a generator;
  a portable radiographic imaging apparatus that includes a first connector that supports a generic communication cable, and a second connector that supports a non-generic communication cable;
  a hardware processor that discriminates a cable connection state to the first connector and the second connector; and
  a radiographing controller that transmits a synchronization signal of starting or finishing irradiation with radiation, to the generator and the portable radiographic imaging apparatus, wherein the hardware processor switches the radiographing controller depending on the discriminated cable connection state.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 5 is a schematic configuration diagram of the radiographic imaging system in a case switched to a type B;

FIG. 6 is a flowchart showing control procedures of a synchronization source switching control process;

FIG. 9 is a schematic configuration diagram of the radiographic imaging system in a case switched to a type C.

DETAILED DESCRIPTION OF THE EMBODIMENTS

Hereinafter, one or more embodiments of the present invention will be described with reference to the drawings. However, the scope of the invention is not limited to the disclosed embodiments.

[Configuration of Portable Radiographic Imaging Apparatus]

Figure 1:
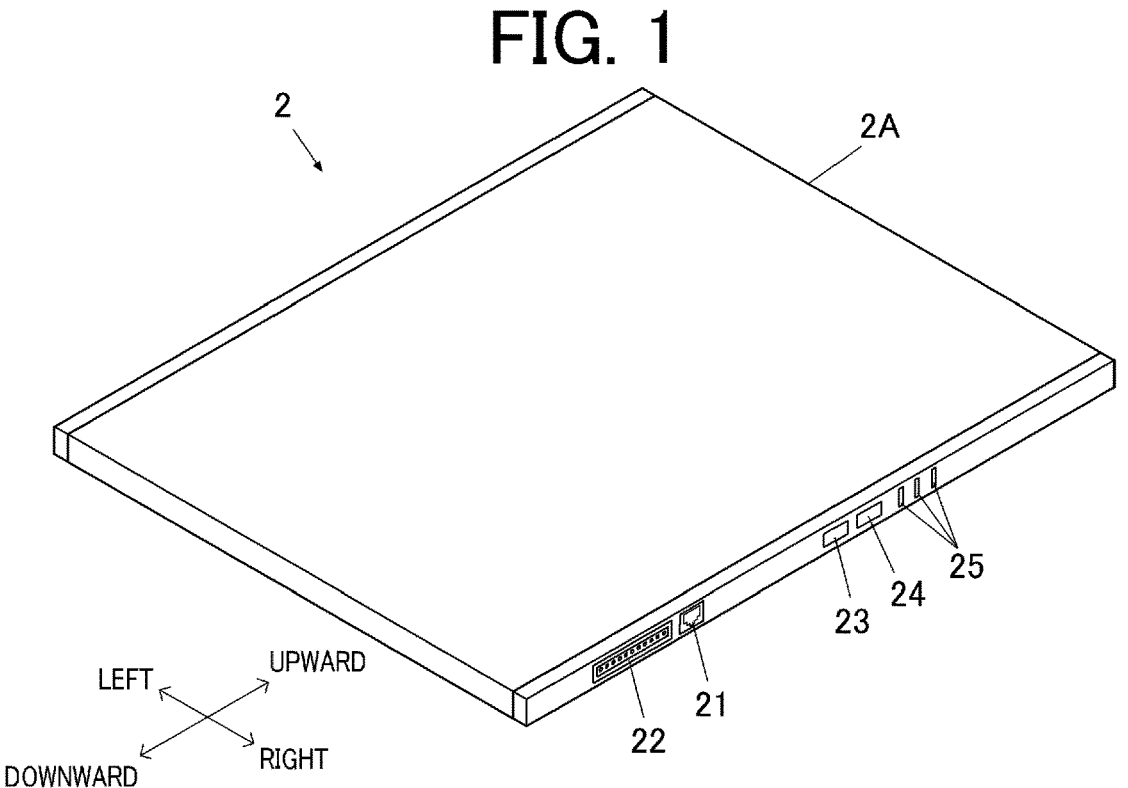
FIG. 1 is a perspective view showing an appearance of a portable radiographic imaging apparatus according to this embodiment.

First, a portable radiographic imaging apparatus according to this embodiment is described. FIG. 1 is a perspective view showing an appearance of the portable radiographic imaging apparatus according to this embodiment.

As shown in FIG. 1, a housing 2A of the portable radiographic imaging apparatus 2 is a plate-shaped rectangular parallelepiped. A first connector 21, a second connector 22, a power source switch 23, a selector switch 24, an indicator 25 and the like are arranged on one side surface (right side surface) of this housing. That is, the first connector 21 and the second connector 22 are thus arranged on a plane perpendicular to an X-ray detection plane (exposure plane) of the portable radiographic imaging apparatus 2. Such aggregation of the first connector 21, the second connector 22, the power source switch 23, the selector switch 24 and the indicator 25 on the one side surface (right side surface) of the housing 2A is intended to allow plugging and unplugging of a cable to the first connector 21 or the second connector 22, user operation to the power source switch 23 and the selector switch 24, and visual identification of the indicator 25, even in a state where the portable radiographic imaging apparatus 2 is stored in a radiographing table (not shown).

The length in the longitudinal direction of the side surface (right side surface) of the housing 2A on which the first connector 21, the second connector 22 and the like are arranged is configured to be the maximum. Such arrangement of the first connector 21, the second connector 22 and the like on the side surface having the maximum length in the longitudinal direction facilitates arrangement of the first connector 21, the second connector 22 and the like.

The first connector 21 is a connector (female connector) that supports a (generic communication cable (e.g., a LAN cable). The generic communication cable is a cable having a connector shape conforming to a communication standard that is typified by USB, LAN, HDMI (R) and the like and is for connection to a PC, a printer and the like. Note that the first connector 21 may be a male connector only if the connector is in a range not hindering the portable radiographic imaging apparatus 2 from being stored in the radiographing table described above.

Figure 2:
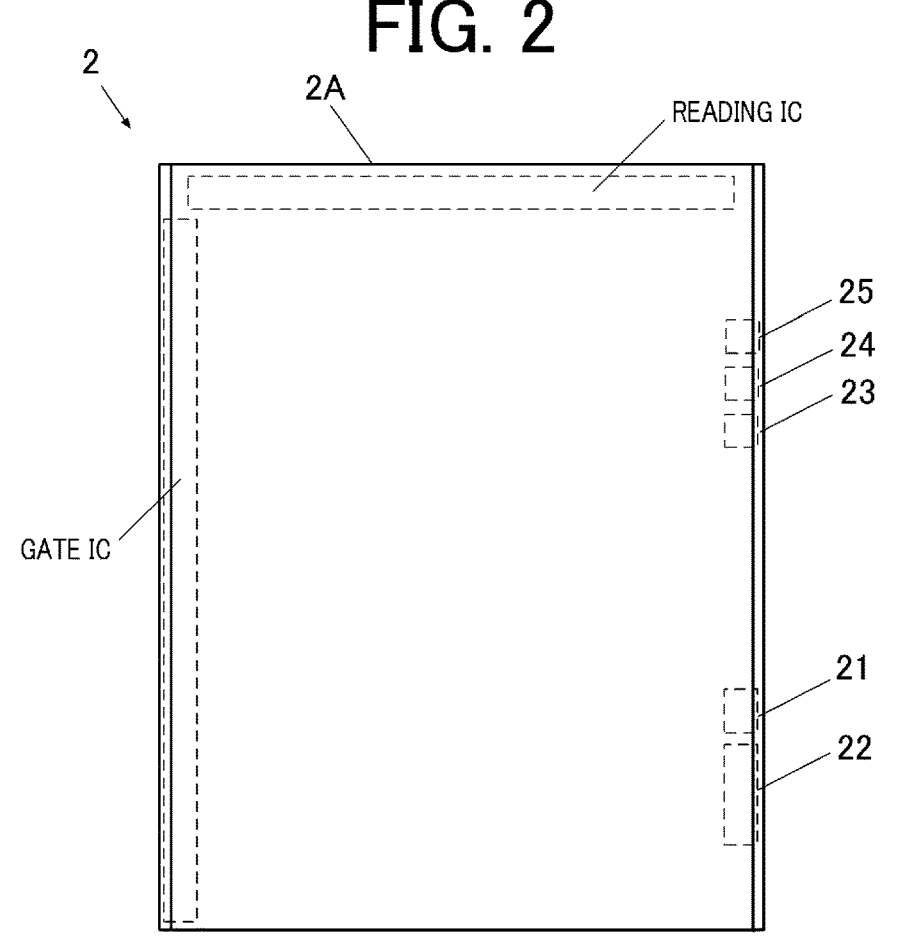
FIG. 2 shows an arrangement of a reading IC and a gate IC in the portable radiographic imaging apparatus.

The first connector 21 is provided at a lower part on the right side surface of the housing 2A. This arrangement is intended to prevent interference with a stopper (not shown) for fixing the portable radiographic imaging apparatus 2 provided on the radiogaphing table when the portable radiographic imaging apparatus 2 is stored in the radiographing table described above. As shown in FIG. 2, the arrangement of the first connector 21 on the right side surface of the housing 2A is because a reading IC is disposed at the top and a gate IC is disposed to the left in the portable radiographic imaging apparatus 2.

The second connector 22 is a connector (female connector) that supports a non-generic communication cable. The non-generic communication cable is a cable having a connector shape that is other than that of the generic communication cable. Note that the second connector 22 may be a male connector only if this connector is in a range not hindering the portable radiographic imaging apparatus 2 from being stored in the radiographing table described above.

The second connector 22 is provided at a position that is at the lower part on the right side surface of the housing 2A and is adjacent to the first connector 21. The arrangement is intended to prevent the second connector 22 from interfering with the stopper described above and to simplify the wiring layout in the portable radiographic imaging apparatus 2. As shown in FIG. 2, the disposition of the second connector 22 on the right side surface of the housing 2A is because the reading IC is disposed at the top and the gate IC is disposed to the left in the portable radiographic imaging apparatus 2.

Figure 3:
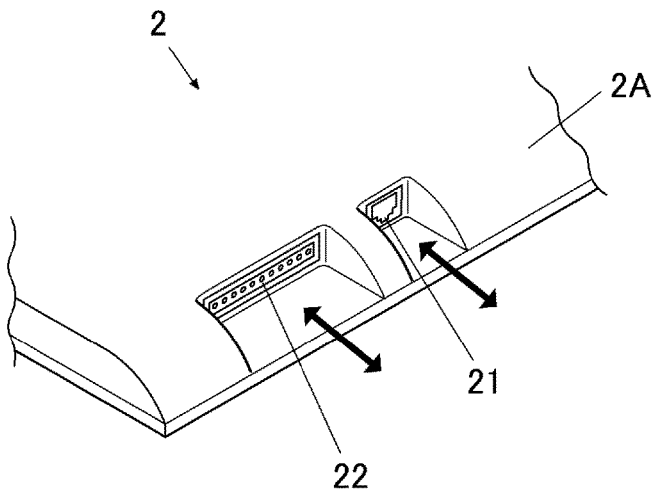
FIG. 3 shows an example of a side view of a housing of the portable radiographic imaging apparatus where a first connector and a second connector are arranged.

Note that as shown in FIG. 3, the side surface of the housing 2A on which the first connector 21, the second connector 22 and the like are arranged may be a curved shape surface continuous to the X-ray detection plane or to the reverse side. Preferably, in this case, the first connector 21 and the second connector 22 are arranged as to allow corresponding cables to be plugged and unplugged in a direction (a direction of each arrow in the diagram) along the X-ray detection plane.

[Configuration of Radiographic Imaging System]

Figure 4:
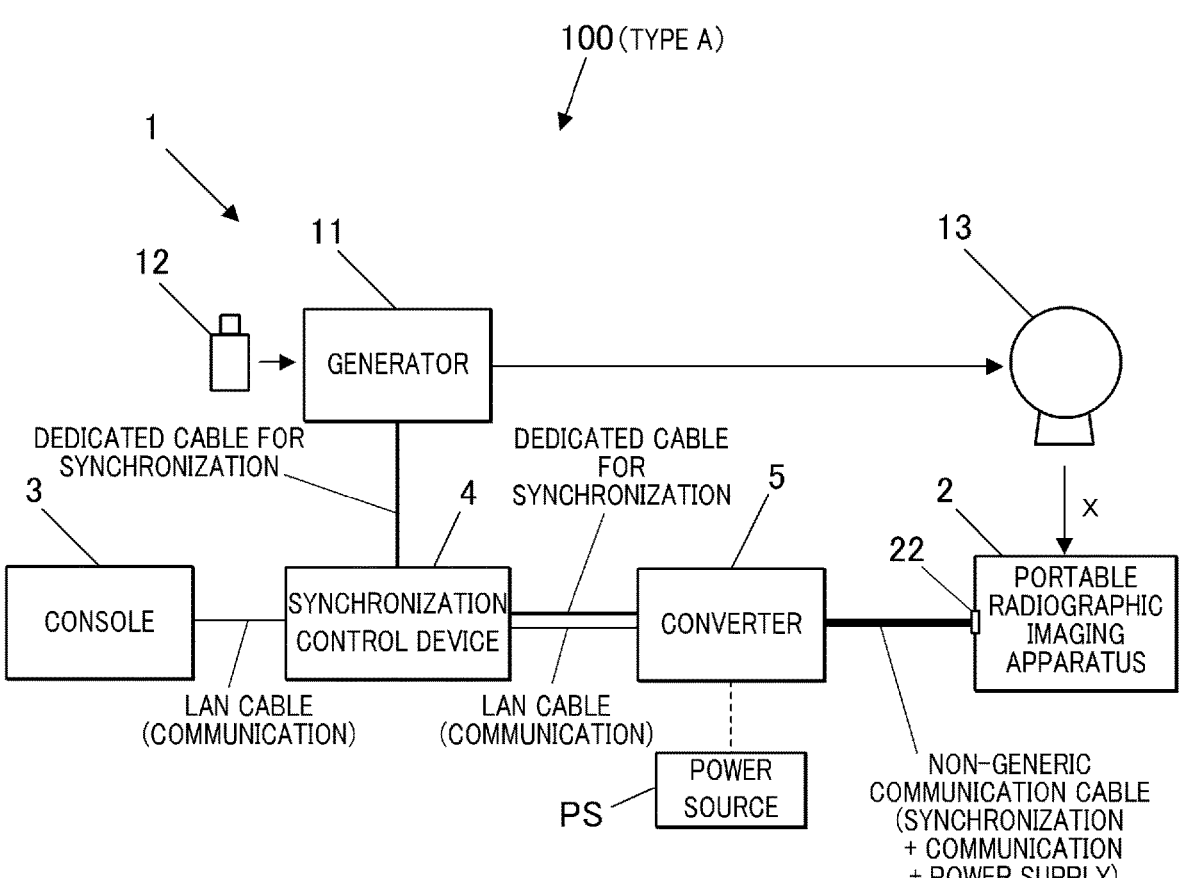
FIG. 4 is a schematic configuration diagram of the radiographic imaging system in a case switched to a type A.

Next, a configuration of a radiographic imaging system according to this embodiment is described. The radiographic imaging system according to this embodiment can be switched to any of a type A (system A) and a type B (system B) and then take a radiograph. FIG. 4 is a schematic configuration diagram of a radiographic imaging system 100 in the case switched to the type A.

As shown in FIG. 4, the radiographic imaging system 100 in the case switched to the type A includes a radiation irradiation apparatus 1, the portable radiographic imaging apparatus 2, a console 3 (hardware processor), a synchronization control device 4 (radiographing controller), and a converter 5.

Note that in the case switched to the type A and also in the case switched to the type B, the radiographic imaging system 100 is connectable to a radiology information system (RIS), a picture archiving and communication system (PACS) and the like, not shown.

The radiation irradiation apparatus 1 includes a generator 11, an exposure switch 12, and a radiation source 13.

The generator 11 is configured to be capable of applying, to the radiation source 13, a voltage according to preset radiation irradiation conditions (the tube voltage, tube current, irradiation time period (mAs value), etc.), based on operation on the exposure switch 12.

The radiation source 13 (tube) includes a rotary anode, a filament and the like, which are not shown. When the voltage is applied by the generator 11, the filament emits an electron beam in accordance with the voltage applied to the filament toward the rotary anode, and this rotary anode generates radiation X (X-rays etc.) having a radiation dose in accordance with the intensity of the electron beam.

FIG. 4 exemplifies the separately configured components 11 to 13, which may be configured in an integrated manner, instead.

FIG. 4 further exemplifies the exposure switch 12 connected to the generator 11. Alternatively, the exposure switch 12 may be included in another apparatus (e.g., an operation console, not shown).

The radiation irradiation apparatus 1 may be installed in a radiological room, or be movably configured by being embedded in an examination car or the like.

The portable radiographic imaging apparatus 2 includes: a radiation detection element that emits charges in accordance with the radiation dose by receiving the radiation X; a substrate on Which pixels including switch elements accumulating and emitting charges are two-dimensionally arranged (in a matrix manner); a reading circuit (a reading IC; see FIG. 2) that reads the amount of charges emitted from each pixel as a signal value; a controller that generates image data from a plurality of signal values read by the reading circuit; and an output device (the first connector 21, the second connector 22, etc.) and the like that wiredly or wirelessly emit the generated image data and the like to the outside.

Note that the portable radiographic imaging apparatus 2 may be what internally includes a scintillator and the like, and causes the scintillator to convert the emitted radiation X into light with another wavelength, such as of visible light, and causes charges in accordance with the converted light (what is called an indirect type), or what directly causes charges from the radiation X without intervention of a scintillator or the like (what is called a direct type).

The console 3 is made up of a PC, a mobile terminal, or a dedicated apparatus, and communicably connected to the radiation irradiation apparatus 1 and the portable radiographic imaging apparatus 2. Specifically, the console 3 is communicably connected to the generator 11 via the synchronization control device 4 (described later). The console 3 is communicably connected to the portable radiographic imaging apparatus 2 via the synchronization control device 4 (described later) and the converter 5 (described later).

The console 3 (a hardware processor) can set various radiographing conditions of the radiation irradiation apparatus 1 and the portable radiographic imaging apparatus 2 (e.g., conditions about a subject, such as a site to be radiographed, and conditions about radiation irradiation, such as the tube voltage or the tube current and the irradiation time period), based on a radiographing order from the external apparatus (RIS etc.) or operation by the user. Note that the radiation source 13 of the radiation irradiation apparatus 1 may be capable of calculating the radiation dose or the patient exposed dose, based on the measurement value of a dose area product (DAP), and be capable of issuing a notification about the calculation result through a UI (display etc.)

The synchronization control device 4 is made up of a computer or a dedicated apparatus, and is communicably connected to the console 3 via a LAN cable, and communicably connected to the generator 11 via a dedicated cable for synchronization. Upon receipt of a control signal of an instruction for taking a radiograph from the console 3, the synchronization control device 4 transmits predetermined synchronization signals (a synchronization signal for starting radiation irradiation, and a synchronization signal for finishing radiation irradiation) to the radiation irradiation apparatus 1 and the portable radiographic imaging apparatus 2, and synchronizes the radiation irradiation apparatus 1 and the portable radiographic imaging apparatus 2 with each other, That is, in the radiographic imaging system 100 in the case switched to the type A, the synchronization control device 4 functions as a synchronization master (radiographing controller).

The converter 5 is a device that integrally combines the synchronization signals input from the synchronization control device 4 and a predetermined communication signal, and a power supplied from a power source PS, and outputs this combination to the portable radiographic imaging apparatus 2. The converter 5 and the synchronization control device 4 are connected by a dedicated cable for synchronization and a LAN cable in parallel. The synchronization signals are input from the synchronization control device 4 to the converter 5 via the dedicated cable for synchronization. Meanwhile, the predetermined communication signal described above is input from the synchronization control device 4 to the converter 5 via the LAN cable. The converter 5 and the portable radiographic imaging apparatus 2 are connected to each other by a non-generic communication cable that supports the second connector 22. The synchronization signals, the predetermined communication signal and the power, which have been integrally combined by the converter 5, are output to the portable radiographic imaging apparatus 2 via the non-generic communication cable. Based on the power input via the non-generic communication cable, the portable radiographic imaging apparatus 2 charges a battery (not shown) that supplies each component with power.

The thus configured radiographic imaging system 100 (type A) connects the synchronization control device 4 and the radiation irradiation apparatus 1 to each other by the dedicated cable for synchronization, connects the synchronization control device 4 and the converter 5 by the dedicated cable for synchronization and the LAN cable in parallel, and connects the converter 5 and the portable radiographic imaging apparatus 2 to each other by the non-generic communication cable, thereby allowing each signal (including power) to be efficiently transmitted. Consequently, the radiographic imaging system 100 (type A) has high consumption power as with dynamic radiographing, and is suitable for taking a radiograph that requires accurate exposure synchronization. Here, dynamic radiographing is repetitive generation of a series of image data items based on the radiation X emitted from the radiation irradiation apparatus 1, by the portable radiographic imaging apparatus 2 repetitively accumulating charges and reading the signal value, based on one radiographing operation (pressing of the exposure switch) multiple times in a short time period (e.g., 15 times per second).

Next, the configuration of the radiographic imaging system 100 in the case switched to the type B is described. FIG. 5 is a schematic configuration diagram of the radiographic imaging system 100 in the case switched to the type B.

As shown in FIG. 5, the radiographic imaging system 100 in the case switched to the type B includes the radiation irradiation apparatus 1, the portable radiographic imaging apparatus 2, and the console 3. Consequently, unlike the radiographic imaging system 100 (type A), the radiographic imaging system 100 (type B) does not include the synchronization control device 4, the converter 5, the dedicated cable for synchronization, the non-generic communication cable and the like. Accordingly, the system cost can be reduced.

The console 3 is communicably connected to the radiation irradiation apparatus 1 and the portable radiographic imaging apparatus 2. Specifically, the console 3 is communicably connected to the generator 11 via a HUB 6 by LAN cables. The console 3 is communicably connected to the portable radiographic imaging apparatus 2 via the HUB 6 by LAN cables.

In the radiographic imaging system 100 in the case switched to the type B, the console 3 transmits predetermined synchronization signals to the radiation irradiation apparatus 1 and the portable radiographic imaging apparatus 2, and synchronizes the radiation irradiation apparatus 1 and the portable radiographic imaging apparatus 2 with each other. That is, in the radiographic imaging system 100 in the case switched to the type B, the console 3 functions as a synchronization master (radiographing controller). Note that in the radiographic imaging system 100 in the case switched to the type B, the portable radiographic imaging apparatus 2 may function as the synchronization master.

In the radiographic imaging system 100 in the case switched to the type B, the portable radiographic imaging apparatus 2 is supplied with power from the power source PS connected via the HUB 6. Here, the portable radiographic imaging apparatus 2 is connected to the HUB 6 by a generic communication cable (LAN cable) that supports the first connector 21. Based on the power input via the LAN cable, the portable radiographic imaging apparatus 2 charges a battery (not shown) that supplies each component with power. The portable radiographic imaging apparatus 2 may be supplied with power according to a wireless power supply scheme.

In the thus configured radiographic imaging system 100 (type B), the radiation irradiation apparatus 1, the portable radiographic imaging apparatus 2, the console 3 and the power source PS are connected to each other via the HUB 6 by the LAN cables that are generic communication cables. Consequently, the radiographic imaging system 100 (type B) has a lower power supply rate than the radiographic imaging system 100 (type A) does. Since the exposure accuracy is low, the power consumption is low, and this system is suitable for taking a radiograph that is a still image without any need of accurate exposure synchronization.

[Operation of Radiographic Imaging System]

Next, a synchronization source switching control process that is performed as part of operation of the radiographic imaging system 100 is described. FIG. 6 is a flowchart showing control procedures of the synchronization source switching control process.

(Synchronization Source Switching Control Process)

As shown in FIG. 6, when the synchronization source switching control process is started, first, the console 3 (the hardware processor, or a discriminator) discriminates the cable connection state of the first connector 21 and the second connector 22 (Step S1).

Next, the console 3 determines whether the cable connection state of the first connector 21 and the second connector 22 is changed or not (Step S2).

If it is determined in Step S2 that the cable connection state of the first connector 21 and the second connector 22 is not changed (Step S2; NO), the console 3 finishes the synchronization source switching control process.

If it is determined in Step S2 that the cable connection state of the first connector 21 and the second connector 22 is changed (Step S2; YES), the console 3 (the hardware processor, or a switcher) switches the synchronization source depending on the cable connection state of the first connector 21 and the second connector 22 (Step S3). Specifically, if cable connection to the second connector 22 is switched to cable connection to the first connector 21, the console 3 switches the synchronization source from the synchronization control device 4 to the console 3. On the other hand, if cable connection to the first connector 21 is switched to cable connection to the Second connector 22, the console 3 switches the synchronization source from the console 3 to the synchronization control device 4.

Figure 7:
FIG. 7 shows an example of a cooperation scheme table.

Next, the console 3 obtains a cooperation scheme table T (see FIG. 7) from a storage (not shown) of this apparatus (Step S4).

Next, the console 3 refers to the cooperation scheme table T obtained in Step S4 and switches the cooperation scheme (Step S5). Specifically, if the cable connection to the second connector 22 is switched to the cable connection to the first connector 21, that is, if the type A is switched to the type B, the console 3 switches the cooperation scheme from a hardware scheme to a software scheme. On the other hand, if the cable connection to the first connector 21 is switched to the cable connection to the second connector 22, that is, if the type B is switched to the type A, the console 3 switches the cooperation scheme from the software scheme to the hardware scheme. The console 3 then finishes the synchronization source switching control process. Here, the cooperation indicates reception of an irradiation start signal from the radiation irradiation apparatus 1, and transmission of an interlock cancel signal from the portable radiographic imaging apparatus 2 to the radiation irradiation apparatus 1. The hardware scheme is a scheme of cooperation through a hardware signal (synchronization pulse signal) in conformity with the specifications of the radiation irradiation apparatus 1. The software scheme is a scheme of cooperation based on a communication command through software.

Figure 8:
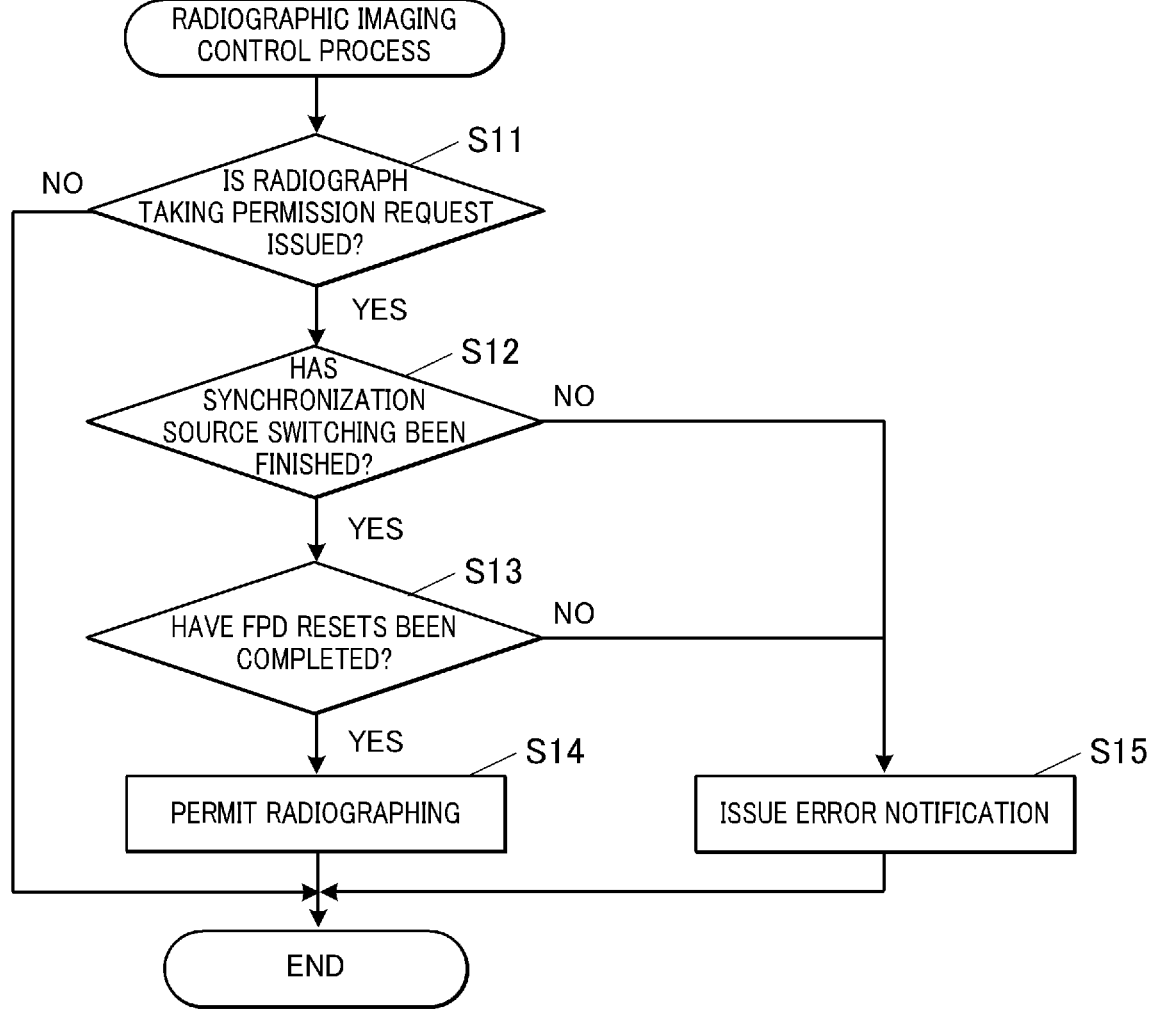
FIG. 8 a flowchart showing control procedures of a radiographic imaging control process.

Next, a radiographic imaging control process that is performed as part of operation of the radiographic imaging system 100 is described. FIG. 8 a flowchart showing control procedures of the radiographic imaging control process.

(Radiographic Imaging Control Process)

As shown in FIG. 8, when the radiographic imaging control process is started, first, the console 3 determines whether a radiograph taking permission request is issued or not (Step S11).

If it is determined in Step S11 that the radiograph taking permission request is not issued in (Step S11; NO), the console 3 finishes the radiographic imaging control process.

If it is determined in Step S11 that the radiograph taking permission request is issued (Step S11; YES), the console 3 determines whether the synchronization source (synchronization master) switching has been finished or not (Step S12).

If it is determined in Step S12 that the synchronization source switching has been finished (Step S12; YES), the console 3 determines whether FPD resets have been completed or not (Step S13). Here, the FPD resets indicate scanning of each pixel of the portable radiographic imaging apparatus 2 (FPD) before taking a radiograph, and removal of unnecessary image signals. The number of resets performed every radiograph taking at the minimum (or a reset time period) may be predefined.

If it is determined in Step S13 that the FPD resets have been completed (Step S13; YES), the console 3 permits the portable radiographic imaging apparatus 2 taking a radiograph (Step S14). The console 3 then finishes the radiographic imaging control process.

If it is determined in Step S12 that the synchronization source switching has not been completed (Step S12; NO) or if it is determined in Step S13 that the FPD resets have not been completed (Step S13; NO), the console 3 issues an error notification by the display (not shown) of this apparatus. The console 3 then finishes the radiographic imaging control process. Note that the error notification described above may be performed by the indicator 25 of the portable radiographic imaging apparatus 2. When the error notification due to incompletion of the synchronization source switching is issued, a notification about a reason of a failure of switching the synchronization source may be issued. When the synchronization source switching is in execution or the FPD reset process described above is in execution, a notification about the fact of being in execution (in switching or in resetting) may be issued, or user operation may be locked (a state of denying acceptance) until the switching is completed.

[Advantageous Effects]

As described above, the portable radiographic imaging apparatus 2 according to this embodiment includes the plurality of connectors to which respective wiring cables are connectable, wherein the plurality of connectors include at least the first connector 21 that supports a generic communication cable, and the second connector 22 that supports a non-generic communication cable.

Consequently, according to the portable radiographic imaging apparatus 2, this portable radiographic imaging apparatus 2 may be usable in the radiographic imaging system 100 (type B; see FIG. 5) using the generic communication cable, and also in the radiographic imaging system 100 (type A; see FIG. 4) using the non-generic communication cable.

In the portable radiographic imaging apparatus 2 according to this embodiment, the first connector 21 and the second connector 22 are disposed on the plane perpendicular to the X-ray detection plane of this apparatus.

Accordingly, even in a state where the portable radiographic imaging apparatus 2 is stored in the radiographing table, the corresponding cable can be smoothly plugged and unplugged.

The portable radiographic imaging apparatus 2 according to this embodiment further includes a battery that supplies power to each component of this apparatus. The battery is rechargeable from the power source PS connected via the first connector 21 and/or the second connector 22.

Accordingly, the portable radiographic imaging apparatus 2 can be supplied with power through the first connector 21 and/or the second connector 22, thus allowing improvement in power supply efficiency.

In the portable radiographic imaging apparatus 2 according to this embodiment, the power source switch 23 and the selector switch 24 that serve as an operation receiver allowing the user to perform predetermined operation, and the indicator 25 serving as the display are arranged on the plane where the first connector 21 and the second connector 22 are arranged.

Accordingly, even in the state where the portable radiographic imaging apparatus 2 is stored in the radiographing table, plugging and unplugging of cables to and from the first connector 21 and the second connector 22, user operation to the power source switch 23 and the selector switch 24, and visual identification of the indicator are allowed.

In the portable radiographic imaging apparatus 2 according to this embodiment, the plane on which the first connector 21 and the second connector 22 are disposed is the plane having the maximum length in this apparatus, thus facilitating arrangement of the first connector 21, the second connector 22, etc.

In the portable radiographic imaging apparatus 2 according to this embodiment, the plane on which the first connector 21 and the second connector 22 are arranged serves a plane where neither the reading IC nor the gate IC is arranged, thus Facilitating arrangement of the first connector 21, the second connector 22, etc.

The radiographic imaging system 100 according to this embodiment includes: the radiation irradiation apparatus 1 that includes the radiation source 13 that generates the radiation X according to the control signal from the generator 11; the portable radiographic imaging apparatus 2 that includes the first connector 21 that supports a generic communication cable, and the second connector 22 that supports a non-generic communication cable; the discriminator (console 3) that discriminates the cable connection state to the first connector 21 and the second connector 22; the radiographing controller (console 3 or the synchronization control device 4) that transmits a synchronization signal of starting or finishing irradiation with the radiation X, to the generator 11 and the portable radiographic imaging apparatus 2; and the switcher (console 3) that switches the radiographing controller depending on the cable connection state discriminated by the discriminator.

Consequently, according to the radiographic imaging system 100, use of the portable radiographic imaging apparatus 2 can switch the system 100 to any of the type A and the type B and use the system 100. Accordingly, a radiograph can be taken appropriately depending on situations.

[Other]

Note that the present invention obviously is not limited to the above embodiment and the like, and alterations can be made, as appropriate, without departing from the gist of the present invention.

For example, in the embodiment described above, the LAN cable is described as an example of the generic communication cable. However, the generic communication cable is not limited to the LAN cable, and may be a USB cable or the like.

In the embodiment described above, the portable radiographic imaging apparatus 2 includes the first connector 21 and the second connector 22 as a plurality of connectors to which wired cables are connectable. However, the number of connectors is not limited to two, but may be three or more.

In the embodiment described above, in the case where the radiographic imaging system 100 is switched to the type A, the portable radiographic imaging apparatus 2 is supplied with power from the power source PS via the non-generic communication cable (see FIG. 4). In the case where the radiographic imaging system 100 is switched to the type B, the portable radiographic imaging apparatus 2 is supplied with power from the power source PS via the LAN cable, which is a generic communication cable (see FIG. 5). A plurality of chargers may be provided for the respective types. Specifically, in the case where the radiographic imaging system 100 is switched to the type A, not only charging via the non-generic communication cable described above, but also any of charging via a dedicated cable for charging, and non-contact charging may be used as the charger. In such a case, in an environment that allows to use the charger described above where the priority of charging via the non-generic communication cable is preset to "high", the priority of charging via the dedicated cable for charging is preset to "medium", and the priority of non-contact charging is preset to "low", the portable radiographic imaging apparatus 2 may be charged according to the priority. In the case where the radiographic imaging system 100 is switched to the type B, any of charging via the dedicated cable for charging, charging via the generic communication cable (LAN cable) described above, and non-contact charging may be used for the charger. In such a case, in an environment that allows to use the charger described above where the priority of charging via the dedicated cable for charging is preset to "high", the priority of charging via the generic communication cable is preset to "medium", and the priority of non-contact charging is preset to "low", the portable radiographic imaging apparatus 2 may be charged according to the priority.

In the embodiment described above, an error guard against a case where corresponding cables are respectively connected to the first connector 21 and the second connector 22 (both plugged) may be provided. According to this error guard, if the corresponding cables are respectively connected to the first connector 21 and the second connector 22, for example, a preset type (the type A or the type B) is set as a switch target. According to another error guard, if a corresponding cable is connected to a connector between the first connector 21 and the second connector 22, electric exclusive control is executed, and connection of any cable to the other connector may be disabled.

In the embodiment described above, an inhibitor that inhibits the cables from being respectively connected to the first connector 21 and the second connector 22 (both plugged) may be provided. As the inhibitor, for example, a slide type shutter (not shown) may be provided for the housing 2A of the portable radiographic imaging apparatus 2. If the first connector 21 is blocked by the shutter, the cable (non-generic communication cable) may be allowed to be connected to the second connector 22. If the second connector 22 is blocked, the cable (generic communication cable) may be allowed to be connected to the first connector 21.

In the embodiment described above, between the case where the radiographic imaging system 100 is switched to the type A, and the case where this system is switched to the type B, a delay occurring during communication of the synchronization signal, and the error range (error tune period) are changed. When radiation is emitted without consideration of such a change, there is a possibility that the irradiation time period is not accommodated in an accumulation time period (a tune period Where the portable radiographic imaging apparatus 2 is in a state where charges can be accumulated), and artifacts, such as an afterimage, a horizontal stripe, and uneven steps occur. Accordingly, in the case of calculating an irradiation time period prescribed value that accommodates an emission start and an emission finish of one radiation pulse by the radiation irradiation apparatus 1 in a predetermined accumulation time period, the hardware processor (a calculator) can calculate the irradiation time period prescribed value in consideration of the delay and error range described above. The hardware processor may be capable of regulating setting of an accumulation time period outside of the calculated irradiation time period prescribed value. The hardware processor may derive a sellable irradiation time period by the following calculation expression.

settable irradiation time period=accumulation time
period−(irradiation time period+delay (including
the error range))

For frame rates where the value of "accumulation time period−delay" is zero or less, an error notification that radiographing is not permitted or the value is zero or less may be issued.

Depending on the delay and the value of the error range (error time period), executability of dynamic radiographing and/or still image taking may be switched. For example, if the delay is smaller than a prescribed value and the error range is narrower than a prescribed value, i.e., if the synchronization accuracy is higher than a prescribed value, dynamic radiographing may be permitted.

In the embodiment described above, the portable radiographic imaging apparatus 2 is charged by being supplied with power from the power source PS. However, when a portable radiograph is taking, occurrence of disturbance noise for the portable radiographic imaging apparatus 2 may be suppressed by suppressing power supply from the power source PS.

In the embodiment described above, the battery provided for the portable radiographic imaging apparatus 2 may be designed to be embedded in the portable radiographic imaging apparatus 2, or may have a detachable structure and be rechargeable using a charging device, not shown.

In the embodiment described above, if the radiographic imaging system 100 is switched to the type A, communication is performed with the outside via the non-generic communication cable connected to the second connector 22.

If the radiographic imaging system 100 is switched to the type B, communication is performed with the outside via the generic communication cable (LAN cable) connected to the first connector 21. Alternatively, communication may be performed with the outside in a wireless scheme via an antenna (not shown) provided for the portable radiographic imaging apparatus 2, instead of the type A or the type B.

In the embodiment described above, the radiographic imaging system 100 is configured to be switchable to any of the type A and the type B. Alternatively, this system may be switchable to a type C that is different from the type A and the type B.

Figure 9:
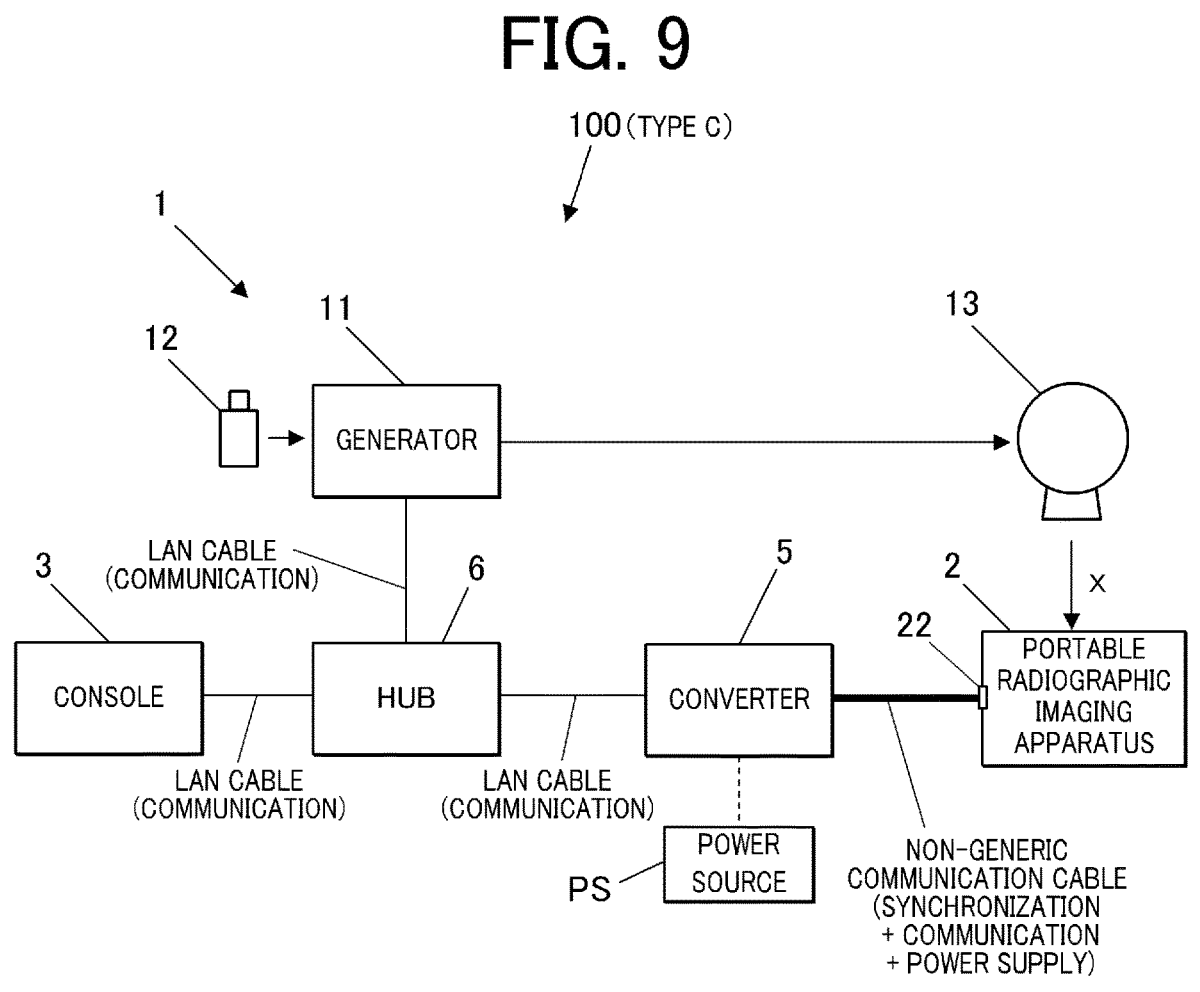

FIG. 9 is a schematic configuration diagram of the radiographic imaging system in the case switched to the type C.

As shown in FIG. 9, the type C is what is called a hybrid type where the type A and the type B are combined. Specifically, the radiographic imaging system 100 in the case switched to the type C includes the radiation irradiation apparatus 1, the portable radiographic imaging apparatus 2, the console 3, and the converter 5. The console 3 is communicably connected to the generator 11 via a HUB 6 by LAN cables. The console 3 is communicably connected to the converter 5 via the HUB 6 by LAN cables. The converter 5 and the portable radiographic imaging apparatus 2 are connected to each other by a non-generic communication cable that supports the second connector 22. The predetermined communication signal (including the synchronization signal) and the power, which have been integrally combined by the converter 5, are output to the portable radiographic imaging apparatus 2 via the non-generic communication cable. Similar to the case of the type B, in the radiographic imaging system 100 in the case switched to the type C, the console 3 transmits predetermined synchronization signals respectively to the radiation irradiation apparatus 1 and the portable radiographic imaging apparatus 2, and synchronizes the radiation irradiation apparatus 1 and the portable radiographic imaging apparatus 2 with each other, The thus configured radiographic imaging system 100 (type C) can reduce the system cost by an amount of negating the need of the synchronization control device 4, the dedicated cable for synchronization, etc., which are used for the type A. By connecting the portable radiographic imaging apparatus 2 and the converter 5 to each other by the non-generic communication cable, each signal (including power) can be efficiently transmitted. Note that it is desirable that similar to the type B, the radiographic imaging system 100 switched to the type C have a cooperation scheme that is of the software scheme.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A portable radiographic imaging apparatus, comprising:

a plurality of connectors to which respective wiring cables are connectable, wherein the plurality of connectors include at least a first connector that supports a generic communication cable, and a second connector that supports a non-generic communication cable, and wherein the generic communication cable and the non-generic communication cable communicate synchronization signals to synchronize with a radiation irradiation apparatus.

2. The portable radiographic imaging apparatus according to claim 1, wherein the first connector and the second connector are disposed on a plane perpendicular to an X-ray detection plane of the apparatus.

3. The portable radiographic imaging apparatus according to claim 1, further comprising:

a battery that supplies power to each component of the apparatus, wherein the battery is rechargeable from an external power source connected via the first connector and/or the second connector.

4. The portable radiographic imaging apparatus according to claim 2, wherein one or more of an operation receiver that allows a user to perform a predetermined operation, and a display is provided on the plane.

5. The portable radiographic imaging apparatus according to claim 2, wherein the plane is a plane that has a maximum length in the apparatus.

6. The portable radiographic imaging apparatus according to claim 2, wherein the plane is a plane on which neither a reading integrated circuit (IC) nor a gate IC is disposed.

\* \* \* \* \*